United States Patent [19]

Carr

[11] 4,178,380

[45] Dec. 11, 1979

[54] BENZOPYRANCARBOXAMIDES

[75] Inventor: John B. Carr, Houston, Tex.

[73] Assignee: Shell Oil Company, Houston, Tex.

[21] Appl. No.: 929,400

[22] Filed: Jul. 31, 1978

Related U.S. Application Data

[63] Continuation-in-part of Ser. No. 778,534, Mar. 17, 1977, abandoned.

[51] Int. Cl.$^2$ .................... A61K 31/35; C07D 311/12
[52] U.S. Cl. ................................ 424/283; 260/345.2; 260/345.5
[58] Field of Search .......................... 260/345.2, 345.5; 424/283

[56] References Cited

U.S. PATENT DOCUMENTS 4,103,021  7/1978  Carr ..................................... 424/283

Primary Examiner—Nicky Chan

[57] ABSTRACT

Novel 3,4-dihydro-N-(2-propenyl)-2H-1-benzopyran-2(or 3)-carboxamides useful as lipogenesis inhibitors in mammals.

10 Claims, No Drawings

BENZOPYRANCARBOXAMIDES

This application is a continuation-in-part of application Ser. No. 778,534, filed on Mar. 17, 1977, now abandoned.

DESCRIPTION OF THE INVENTION

It has been found that lipogenesis in mammals is inhibited by novel 3,4-dihydro-N-(2-propenyl)-2H-1-benzopyran-2(or 3)-carboxamides, described by the formula

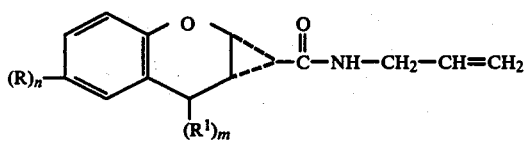

wherein n is zero or one, R is halogen; nitro; amino; trifluoromethyl; methylsulfonylamino; alkyl or alkoxy of from one to six carbon atoms; cycloalkyl of from three to six carbon atoms; phenyl, phenoxy, benzyl or 2-phenethyl, or any of these substituted by one or two of one or more of alkyl of from one to six carbon atoms, halogen and nitro; m is zero or one, and $R^1$ is hydroxyl, with the proviso that when m is one, the compound is in the cis isomeric configuration. By halogen is meant chlorine, fluorine, bromine and iodine, the middle halogens, bromine and chlorine, being preferred. Each alkyl moiety may be of straight-chain or branched-chain configuration.

In Formula I, the dotted lines from the free bond of the aminocarbonyl moiety to the carbon atoms in the 2- and 3-positions of the ring structure indicate that the contemplated compounds include those wherein the aminocarbonyl moiety is bonded to the ring at the 2-position, as well as those in which that moiety is bonded to the ring at the 3-position.

With respect to those compounds of Formula I wherein $R^1$ is hydroxyl, the preparative method is such that essentially only the cis isomeric configuration results.

Chirality exists in the compounds of Formula I due to the asymmetric structural configuration at the carbon atom to which the aminocarbonyl moiety is bonded. As a result, two optical isomers of the compounds of Formula I exist. At the time this application is filed, no attempt has been made to separate and determine the lipogenesis inhibition activity of the individual optical isomers. Under the circumstances, the invention contemplates the individual active optical isomers, as well as mixtures thereof.

For illustration, preparation of typical individual species of the genus defined by Formula I are described in the examples included hereinafter. Other typical, illustrative individual species of this genus are those wherein n=1, the aminocarbonyl moiety is at the 2-position of the ring, and R=
 fluoro
 trifluoromethyl
 methoxy
 nitro
 amino
 methylsulfonylamino n=1, the aminocarbonyl moiety is at the 3-position of the ring, and R=
 methoxy
 amino
 methylsulfonylamino Compounds of this genus wherein m is zero can be prepared by treating the appropriate corresponding carboxylic acid chloride with 2-propenamine.

The acid chloride precursors can be prepared by treating the corresponding carboxylic acids with thionyl chloride. An excess of the thionyl chloride is used, part acting as solvent. Conveniently, the treatment is conducted by refluxing the mixture. The excess thionyl chloride then is evaporated, leaving the acid chloride crude product, from which the acid chloride can be isolated by conventional means.

The acid chloride—either the crude or isolated product—then is treated with an excess of the amine, a solvent, such as methylene chloride, being added if needed to moderate the reaction and/or to ensure a liquid reaction medium. The amide product can be recovered and isolated from the reaction mixture by conventional means.

The carboxylic acid and ester precursors are in part a known class of compounds: Witiak et al., J. Med. Chem., 14, 758–66 (1971); Witiak et al., J. Med. Chem., 18, 934–42 (1975); Taylor et al., J. Chem. Soc. London, 1950, 2724–5.

Compounds of the invention also can be prepared by heating an alkyl, suitably methyl or ethyl, ester of the corresponding carboxylic acid, in solution in a suitable solvent such as ethanol, with 2-propenamine. While the reaction can be effected at somewhat lower temperatures, suitably it can be conducted efficiently by refluxing the mixture. Preferably, about a four-to-six fold excess of the amine is used. The desired product can be recovered by evaporating the solvent and excess amine, then employing conventional techniques, such as selective extraction, recrystallization and/or dry-column chromatography, to isolate the desired product.

Those carboxylic acids and esters which are not shown in the cited art can be prepared by analogous methods:

(a) those acids wherein the carboxy moiety is bonded at the 2-position of the ring and R is other than phenyl, alkyl or cycloalkyl can be prepared by treating the appropriate 4-R-phenol with alpha-bromogamma-butyrolactone to form the 3-(4-R-phenoxy)dihydro-2(3H)-furanone; treating that furanone with Jones reagent to form the 2-(4-R-phenoxy)butanedioic acid; cyclizing that acid with sulfuric acid to form the 6-R-3,4-dihydro-4-oxo-2H-1-benzopyran-2-carboxylic acid and reducing it (zinc-mercury amalgam, hydrochloric acid) to the desired carboxylic acid precursor. Preparation of the precursor ester wherein R is phenyl and is cyclohexyl respectively, is described in Witiak et al., (1975) supra. Where R is alkyl, the presursor acids can be prepared from the 6-alkyl-4-oxo-4H-1-benzopyran-2-carboxylic acids whose preparation is described by Niviere, P., et al., Bull. Soc., Chim. France, 1965, (3658–62).

(b) those esters wherein the alkoxycarbonyl moiety is to be bonded at the 3-position of the ring can be prepared by treating the appropriate salicylaldehyde with acrylonitrile (aqueous sodium hydroxide) to form the 6-R-3,4-dihydro-4-hydroxy-2H-1-benzopyran-3-carbonitrile, which is heated with methanol and hydrochloric acid to form the methyl ester of the 6-R-2H-1- benzopyran-3-carboxylic acid, which is hydrogenated (hydrogen, ethanol, 10% palladium-on-carbon catalyst) to form the ester precursor.

In those compounds wherein $R^1$ is hydroxyl, the precursor acid can be prepared by treating the intermediate 3,4-dihydro-4-oxo-2H-1-benzopyran-2-carboxylic acid alkyl ester with sodium borohydride.

The R=nitro precursor ester can be prepared by nitrating the R=H acid precursor (Witiak et al. (1971) supra), according to the precedure described in Brancaccio et al., J. Heterocyclic Chemistry, 10, 623 (1973), then esterifying the acid by refluxing it in ethanol containing a small amount of sulfuric acid as catalyst.

The R=amino precursor ester can be prepared by reduction of the R=nitro precursor ester, by hydrogenating that ester in ethanol solution containing a 10% palladium-on-carbon catalyst.

The R=methylsulfonylamino ester precursor can be prepared by treating a methylene chloride solution of the R=amino precursor ester containing an equimolar amount of triethylamine with an equimolar amount of methanesulfonyl chloride.

These procedures for preparing compounds of this invention are illustrated in Examples 1–9, following. In all cases, the identities of the products, and of the precursors involved were confirmed by appropriate chemical and spectral analyses.

EXAMPLE 1

6-Chloro-3,4-dihydro-N-(2-propenyl)-2H-1-benzopyran-2-carboxamide (1)

A solution of 3.1 g of 6-chloro-3,4-dihydro-2H-1-benzopyran-2-carboxylic acid (1A) (Witiak et al. (1971), supra) in 15 ml of thionyl chloride was refluxed for 45 minutes. The excess thionyl chloride then was stripped off and the residual liquid taken up in 50 ml of methylene chloride. To this stirred solution was added dropwise a solution of 2.5 g of 2-propenamine in 10 ml of methylene chloride. The resulting mixture was stirred at room temperature overnight, then was washed with water, dried (MgSO$_4$) and stripped of solvent. Dry column chromatography of the solid product through silica gel, using Solvent No. 3 (a 4:30:66 by volume mixture of tetrahydrofuran, ethyl acetate and hexane) as eluent, followed by recrystallization of the product from ethylene chloride and hexane gave 1, as a pale yellow solid, mp: 112.5°–114° C. Example 2

3,4-Dihydro-N-(2-propenyl)-2H-1-benzopyran-3-carboxamide (2)

A solution of 10.4 g of the methyl ester of 2H-1-benzopyran-3-carboxylic acid (Taylor et al., supra) in 50 ml of methanol containing 300 mg of 10% palladium-on-carbon catalyst was hydrogenated in a Parr apparatus for 1.5 hours, at an initial pressure of 44 psig. The mixture then was filtered through a Celite pad, the filtrate was stripped of solvent, and the product was vacuum distilled to give the methyl ester of 3,4-dihydro-2H-1-benzopyran-3-carboxylic acid (2A), as a colorless liquid, bp: 86°–88° C. (0.01 Torr.).

A solution of 5 g of 2A and 5.7 g of 2-propenamine in 50 ml of ethanol was refluxed for 6 days. Stripping of the solvent, followed by charcoal treatment of the product and recrystallization of the treated product from ether-hexane, gave 2, as white crystals, mp: 114.5°–115.5° C.

EXAMPLE 3

3,4-Dihydro-N-(2-propenyl)-2H-1-benzopyran-2-carboxamide (3)

3 Was prepared as white crystals, mp: 76°–77° C. from the ethyl ester of chroman-2-carboxylic acid (Witiak et al. (1971)) and 2-propenamine, by the procedure described in the last paragraph of Example 2.

EXAMPLE 4

3,4-Dihydro-6-phenyl-N-(2-propenyl)-2H-1-benzopyran-2-carboxamide (4)

4 Was prepared as a white solid, mp: 123°–124° C. from the ethyl ester of 3,4-dihydro-6-phenyl-2H-1-benzopyran-2-carboxylic acid (Witiak et al. (1975)) and 2-propenamine by the procedure described in the last paragraph of Example 2.

EXAMPLE 5

6-Cyclohexyl-3,4-dihydro-N-(2-propenyl)-2H-1-benzopyran-2-carboxamide (5)

5 Also was prepared, as white crystals, mp: 93°–94° C., by the procedure described in the last paragraph of Example 2, from the ethyl ester of 6-cyclohexyl-3,4-dihydro-2H-1-benzopyran-2-carboxylic acid (Witiak et al. (1975)) and 2-propenamine.

EXAMPLE 6

6-Chloro-3,4-dihydro-N-(2-propenyl)-2H-1-benzopyran-3-carboxamide (6)

To a stirred, refluxing mixture of 50 g of 3-chloro-6-hydroxybenzaldehyde and 62 ml of acrylonitrile in 50 ml of water was added dropwise over a three-hour period a solution of 12.8 g of sodium hydroxide in 120 ml of water. Then an additional 62 ml of acrylonitrile was added and the stirred mixture was refluxed for 2 hours, then allowed to stand at room temperature overnight. The crystals which formed were filtered off, washed with water and dried to give a solid, which was recrystallized from ethanol to give 6-chloro-3,4-dihydro-4-hydroxy-(2H)-1-benzopyran-3-carbonitrile (6A), a solid. A mixture of 6A with 250 ml of methanol containing 2 ml of sulfuric acid was refluxed for 4 days and stripped of solvent. The resulting residue was dry column chromatographed over silica gel, using Solvent No. 3 as eluent. The product obtained on workup was rechromatographed and recrystallized from ether to give methyl 6-chloro-2H-1-benzopyran-3-carboxylate (6B), as light yellow needles, mp: 106°–109° C.

700 mg of 6B was dissolved in 75 ml of ethyl acetate and the solution was treated with hydrogen (initial pressure of 30 psig), in the presence of a 10% palladium-on-carbon catalyst, for 8 hours. The reaction mixture then was filtered and stripped of solvent to give methyl 6-chloro-3,4-dihydro-2H-1-benzopyran-3-carboxylate (6C), as a yellow liquid, boiling point not determined.

A mixture of 500 mg of 6C, 5 ml of 2-propenamine and 25 ml of ethanol was refluxed for 18 hours. The sovlent was then stripped off and the residue was taken up in methylene chloride, triturated with hexane and cooled to give a solid. The solid was redissolved in ethanol, the solution was passed through a short silica gel column and the eluent was stripped of solvent. The residue was recrystallized from methylene chloride/hexane to give 6, as white needles, mp: 171°–171.5° C.

EXAMPLE 7

6-Chloro-4-hydroxy-N-(2-propenyl)-2H-1-benzopyran-2-carboxamide (cis) (7)

A solution of 512 mg of the ethyl ester of 6-chloro-3,4-dihydro-4-hydroxy-2H-1-benzopyran-2-carboxylic acid, (prepared by treating the ethyl ester of 6-chloro-3,4-dihydro-4-oxo-2H-1-benzopyran-2-carboxylic acid (Witiak et al., supra) with sodium borohydride), 570 mg of 2-propenamine and 20 ml of ethanol was stirred at room temperature for 72 hours, then stirred for 3 hours while heated by a steam bath. The solvent was stripped off and the residue was crystallized from methylene chloride/hexane to give 7, as white crystals, mp: 129°–130.5° C.

EXAMPLE 8

3,4-Dihydro-6-phenoxy-N-(2-propenyl)-2H-1-benzopyran-2-carboxamide (8)

8 was prepared as cream-colored crystals, mp: 104°–106° C., from the ethyl ester of 3,4-dihydro-6-phenoxy-2H-1-benzopyran-2-carboxylic acid (Witiak, et al. (1975)) by the procedure described in the last paragraph of Example 2.

EXAMPLE 9

3,4-Dihydro-6-methyl-N-(2-propenyl)-2H-1-benzopyran-2-carboxamide (9)

6-Methyl-4-oxo-4H-1-benzopyran-2-carboxylic acid (Niviere, et al., 1965) was hydrogenated over a palladium-on-carbon catalyst to give 3,4-dihydro-6-methyl-2H-1-benzopyran-2-carboxylic acid. This acid was converted to the acid chloride with thionyl chloride and the acid chloride was converted to 9, obtained as white plates, mp: 67°–67.5° C., by treatment with 2-propenamine, all by the procedures described in Example 1.

The carboxamides of Formula I have been found to inhibit lipogenesis in mammalian tissues. The manner in which they cause this effect is not known with certainty; it is believed that they interfere with the synthesis of fatty acids in the tissues. Their effectiveness for this purpose has been ascertained by immersing samples of mammalian liver or adipose tissue in a liquid medium containing radioactive glucose and the test chemical for a period of time, then isolating the lipid from the treated tissue and determining the incorporation of the radioactive carbon into the lipid by means of scintillation counting techniques. These tests were conducted with both liver and adipose tissues, because in some animals the primary site of lipogenesis appears to be liver tissue, while in others it appears to be adipose tissue. The test animals were pigs, sheep, rabbits, cats and dogs.

Described in more detail, the tests were conducted according to the following general procedure:

Tissue slices (200 milligrams for liver; 150 milligrams for adipose tissue) were incubated, at 37° C. for 2 hours with shaking in 3 milliliters of Krebs-Ringer bicarbonate solution containing one-half the normal calcium ion concentration, 60 micromoles of glucose, 0.5 micro-Curie of glucose-U-$^{14}$C, 300 microunits of insulin, and 5% dimethyl sulfoxide (DMSO). The test compounds were added as a solution or a suspension in DMSO and were present at a concentration of 100 micrograms per milliliter of the incubation mixture.

The incubation was terminated by addition of 0.25 milliliter of 1 N sulfuric acid. The incubation mixture was extracted with a total of 25 milliliters of chloroform:methanol (2:1, v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained was calculated the percent inhibition of lipid synthesis by the test compound in each case.

Compound 2 was tested with respect to all of the animals. The other six compounds were tested only with respect to the pig.

From these and other tests, it was established that in pigs there is little lipogenic activity in the liver tissue. From these and other tests, it also has been established that swine adipose tissue utilizes glucose for lipogenesis, and to be the major site of fatty acid synthesis. The data obtained from the tests using adipose tissue and glucose are set out in Table 1, as the percent inhibition of lipogenesis compared to the results obtained in the control tests wherein only the test compound was omitted.

TABLE I

| Compound No. | Percent Inhibition |
| --- | --- |
| 1 | 59 |
| 2 | 83 |
| 3 | 72 |
| 4 | 76 |
| 5 | 40 |
| 6 | 67 |
| 7 | 55 |
| 8 | 64 |
| 9 | 70 |

With respect to sheep, both tissues had relatively low rates of lipogenesis. The liver incorporated more glucose into lipids than did the adipose tissue. Compound 2 inhibited (32%) glucose incorporation in the liver and (36%) in adipose tissue.

With respect to rabbits, compound 2 inhibited (9%) glucose incorporation into liver and (22%) in adipose tissue.

With respect to cats, compound 2 caused 26% inhibition of glucose utilization in the liver and did not inhibit glucose utilization in adipose tissue.

With respect to dogs, adipose tissue was considerably more active as a lipogenic tissue than was liver tissue. Compound 2 caused 73% inhibition of glucose utilization in adipose tissue.

The effect of compound 2 on inhibition of lipogenesis in swine was confirmed by an in vivo test in which Compound 2 was included in the the feed given to young, growing pigs for seven days, at a dosage of approximately 50 milligrams of Compound 2 per kilogram of the pig's body weight per day. Adipose tissue biopsy samples were taken at days 0, 6, 7 and 13 (one week off the drug) and the effect of the test compound on lipogenesis was determined using tissue slices prepared from the biopsy samples, by the procedure used in the in vitro tests. Statistical analysis of the results indicated that at day 13 Compound 2 had significantly reduced lipogenesis. No symptom of toxicity due to the test compound was noted.

The carboxamides of Formula I can be used to control lipogenesis in mammals such as, for example, pets, animals in a zoo, livestock, fur-bearing animals and domestic animals, including, but not limited to dogs, cats, mink, sheep, goats, swine, cattle, horses, mules and donkeys. The effect is obtained by administering an effective amount of one or a mixture of two or more of the carboxamides orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug.

Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the carboxamide needed to inhibit lipogenesis will depend upon the particular carboxamide used, and the particular animal being treated. However, in general, satisfactory results are obtained when the carboxamides are administered in a dosage of from about 1 to 500 milligrams per kilogram of the animal's body weight. The carboxamide can be administered in a single dose or in a series of doses in the same day, or over a period of days. For any particular animal, a specific dosage regimen should be adjusted according to the individual need, the particular carboxamide(s) used as the inhibitor, and the professional judgment of the person administering or supervising the administration of the inhibitor. It is to be understood that the dosages set forth herein are exemplary only, and that they do not, to any extent, limit the scope of practice of the invention.

I claim:

1. A compound of the formula

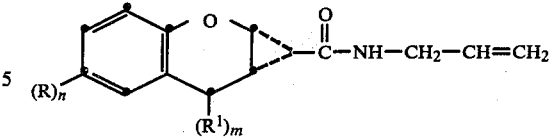

wherein n is zero or one, R is halogen; nitro; amino; trifluoromethyl; methylsulfonylamino; alkyl or alkoxy of from one to six carbon atoms; cycloalkyl of from three to six carbon atoms; phenyl, phenoxy, benzyl or 2-phenethyl, or any of these substituted by one or two of one or more of alkyl of from one to six carbon atoms, halogen and nitro; m is zero or one, and $R^1$ is hydroxyl, with the proviso that when m is one, the compound is in the cis isomeric configuration, the dotted lines indicating that 2-propenylaminocarbonyl moiety is bonded to the benzopyran ring at the 2-position or at the 3-position.

2. A compound according to claim 1 wherein m and n are both zero.

3. A compound according to claim 1 wherein m is zero, n is 1 and R is halogen.

4. A compound according to claim 1 wherein m is zero, n is 1 and R is phenyl.

5. A compound according to claim 1 wherein m is zero, n is 1 and R is phenoxy.

6. A compound according to claim 1 wherein m is zero, n is 1, and $R^1$ is methyl.

7. A method for inhibiting lipogenesis in a mammal, which comprises administering to a mammal in need of such treatment, orally or parenterally, an effective amount of a compound defined in claim 1.

8. A method according to claim 7 wherein m and n are both zero.

9. A method according to claim 7 wherein m is zero, n is 1 and R is halogen.

10. A method according to claim 7 wherein m is zero, n is 1 and R is phenyl.